(12) United States Patent
Wisniewski et al.

(10) Patent No.: US 6,821,504 B2
(45) Date of Patent: Nov. 23, 2004

(54) DETECTION OF ALZHEIMER'S AMYLOID BY MAGNETIC RESONANCE IMAGING

(75) Inventors: Thomas Wisniewski, Staten Island, NY (US); Daniel Turnbull, Larchmont, NY (US); Einar Sigurdsson, New York, NY (US); Youssef Zaim Wadghiri, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/151,614

(22) Filed: May 23, 2002

(65) Prior Publication Data

US 2003/0147811 A1 Aug. 7, 2003

Related U.S. Application Data

(60) Provisional application No. 60/292,625, filed on May 23, 2001.

(51) Int. Cl.$^7$ .................. A61K 51/00; A61M 36/14
(52) U.S. Cl. ............. 424/1.69; 424/1.11; 424/1.65; 424/9.1; 424/9.3
(58) Field of Search ................ 424/1.11, 1.65, 424/1.69, 9.1, 9.2, 9.3, 9.341, 9.35, 9.351; 530/300, 324–330

(56) References Cited

U.S. PATENT DOCUMENTS

| | | | |
|---|---|---|---|
| 5,434,050 A | 7/1995 | Maggio et al. | |
| 5,670,477 A | 9/1997 | Poduslo et al. | |
| 5,721,106 A | 2/1998 | Maggio et al. | |
| 5,837,473 A | * 11/1998 | Maggio et al. | ........... 435/7.21 |
| 6,207,153 B1 | 3/2001 | Dan et al. | |
| 6,471,960 B1 | * 10/2002 | Anderson | ............... 424/94.64 |

OTHER PUBLICATIONS

Selkoe, Dennis J. "Imaging Alzheimer's Amyloid," *Nature Biotechnology*, vol. 18, Aug., *2000* (pp. 823–824).

Fox, N.C. and M.N. Rossor. Seeing What Alzheimer Saw–with Magnetic Resonance Microscopy, *Nature Medicine*, vol. 6, No. 1, Jan., 2000 (pp. 20–21).

Curtet, Chantal, Ph.D. et al. Polylysine–Gd–DTPA$_n$and Polylysine–Gd–DOTA$_n$Coupled to Anti–CEA F(ab')$_2$ Fragments as Potential Immunocontrast Agents,' *Investigative Radiology*, vol. 33, No. 10, Oct., 1998 (pp. 752–761).

Skovronsky, Daniel M. "In Vivo Detection of Amyloid Plaques in a Mouse Model of Alzheimer's Disease," *PNAS*, Jun. 20, 2000, vol. 97, No. 13, (pp. 7609–7614).

Benveniste, Helene et al. "Detection of Neuritic Plaques in Alzheimer's Disease by Magnetic Resonance Microscopy," *PNAS*, Nov. 23, 1999, vol. 96, No. 24, (pp. 14079–14084).

Wengenack, Thomas M. et al. "Targeting Alzheimer Amyloid Plagues in Vivo," *Nature Biotechnology*, vol. 18, Aug., 2000, (pp. 868–872).

Soto, Claudio et al. "Inhibition of Alzheimer's Amyloidosis by Peptides that Prevent β–Sheet Confirmation," *Biochemical and Biophysical Research Communications*, 226, 1996, article No. 1413, (pp. 672–680).

Sigurdsson, Einar M. et al. "In Vivo Reversal of Amyloid–β Lesions in Rat Brain," *Journal of Neuropathology and Experimental Neurology*, vol. 59, No. 1, Jan., 2000, (pp. 11–17).

Gibby, Wendell A., *MRI Contrast Agents*, (pp. 313–364).

Maggio, John E. et al. "Reversible In Vitro Growth of Alzheimer Disease β–Amyloid Plaques by Deposition of Labeled Amyloid Peptide," *Proc. Natl. Acad. Sci. USA*, vol. 89, Jun. 1992, (pp. 5462–5466).

Dhenian, Marc. "Senile Plaques Do Not Induce Susceptibility Effects in T$_2$–Weighted MR Microscopic Images," *NMR Biomed.*, 2002; 15 (pp. 197–203).

* cited by examiner

*Primary Examiner*—Dameron L. Jones
(74) *Attorney, Agent, or Firm*—Browdy and Neimark, P.L.L.C.

(57) ABSTRACT

Alzheimer's disease can be diagnosed in vivo using magnetic resonance imaging. A labeled Aβ peptide or its derivative is injected into the patient to be diagnosed, after which the patient is subjected to magnetic resonance imaging. Both pre-amyloid and amyloid plaques can be detected using this method.

36 Claims, 5 Drawing Sheets

1. Synthesis and characterization of Aβ-specific ligands for µMRI:

2. MR contrast Agent Tagging:

Chelation:

Absorption:

3. µMRI of peptides

4. In vivo intra-carotid injection, of peptides with mannitol

APP Tg
PS1/APP Tg
Or wild-type Mouse

5. In vivo µMRI or µMRI of extracted, whole brains

SEQUENCE LISTING

```
<160> NUMBER OF SEQ ID NOS: 1

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40
```

DETECTION OF ALZHEIMER'S AMYLOID BY MAGNETIC RESONANCE IMAGING

CROSS-REFERENCE TO RELATED APPLICATION

The present application claims priority from Serial No. 60/292,625, filed May 23, 2001, the entire contents of which are hereby incorporated by reference.

GOVERNMENT INTEREST

This invention was made with the support of grants numbers AG-15408 and NS-38461 from the National Institutes of Health. The government has certain rights in the invention.

FIELD OF THE INVENTION

The present invention relates to a method for detecting Alzheimer's disease in vivo using magnetic resonance imaging.

BACKGROUND OF THE INVENTION

Alzheimer's disease is a widespread progressive dementia afflicting a signification proportion of the elderly population. While there has been significant research into the causes and treatment of Alzheimer's disease, the primary pathology of the disorder remains unknown. The behavioral symptoms of Alzheimer's disease are well known, and include loss of memory and cognitive function. The salient pathological symptom of Alzheimer's disease at autopsy is the presence in certain brain areas of extracellular proteinaceous deposits or plaques called amyloid on the basis of their staining with various reagents.

To date, a definitive diagnosis of Alzheimer's disease requires histopathological examination of brain tissue, usually at autopsy. The diagnosis is confirmed by the presence of amyloid plaques in sufficient numbers. Diagnostic clinical criteria have been developed for the disease, and when these are applied in research centers, diagnostic accuracy approaches 90%.

Unfortunately, there are no specific diagnostic tests for Alzheimer's disease, and clinical diagnosis is most difficult in the earliest stages of the disease, when the few available treatments would be most helpful. There is a great need for reliable in vivo non-invasive diagnostic markers of disease and of disease progression. Of course, the most important would be non-invasive measurement of plaques and tangles within the brain. The need for such a methodology has become all the greater recently, with the development of several potential treatment strategies that enhance amyloid clearance. These are being tested in animals or are in Phase I clinical trials currently. For greatest efficacy, these methods will require the definitive identification of patients at early or pre-clinical stages of the disease and a method for monitoring amyloid burden.

In the absence of any method for detecting the histopathological hallmarks of the disease, short of cerebral biopsy, there have been a number of attempts to develop in vivo diagnostic techniques. Generally, these have involved imaging downstream events, such as metabolic changes with functional imaging, or cell loss with structural imaging. Structural imaging, computed tomography or magnetic resonance imaging, is now routinely used in clinical practice when a patient is suspected of having Alzheimer's disease. Magnetic resonance imaging provides higher resolution and better tissue contrast than computed tomography, and may show characteristic hippocampal atrophy. Serially acquired magnetic resonance scans show accelerated cerebral tissue loss in Alzheimer's disease relative to normal ageing. However, although these imaging techniques may help to distinguish the patient with a degenerative cause for the cognitive impairment from a normal control, they are much less specific at identifying the underlying molecular pathology.

Benveniste et al., in Proc. Natl. Acad. Sci. USA 96, 14079–14084 (1999) have applied magnetic resonance imaging, which has proven successful for detecting macroscopic changes such as atrophy, to the detection of microscopic molecular pathology. The potential targets for magnetic resonance microscopy are the plaques and tangles initially seen by Alois Alzheimer when he first diagnosed this disease. However, Benveniste et al. did not use a contrast agent, and to achieve the required resolution of $5.9 \times 10^{-5}$ $\mu$m, scanning times of about 20 hours were needed, something that is not feasible for in vivo studies. Furthermore, a recent attempt to reproduce these findings using even better MRI resolution on brain samples from AD patients, concluded that amyloid could not be imaged directly (Dhenain et al., NMR Biomed. 15: 197–203, 2002).

The magnetic resonance microscopy techniques Benveniste et al. used involved a 7-T machine with coils of 1 cm to image formalin-fixed tissue sections 1 cm in diameter. To visualize the plaques, the contrast-to-noise ratio must be maximized. Two acquisition techniques were used for this: diffusion weighted imaging and T2 imaging. Diffusion-weighted imaging, which measures how well water can undertake Brownian motion, did not show the plaques, suggesting that the plaques did not provide a substantial obstruction to the movement of water molecules. T2 imaging, which measures local perturbations to the applied magnetic field, did show some plaques, but, as noted above, required a resolution of $5.9 \times 10^{-5}$ mm$^3$ and required scanning times of about 20 hours. Such long scanning times would not be feasible in vivo. In addition, this imaging was performed on excised tissue, not intact brains.

The neurofibrillary tangles are intraneuronal aggregates of abnormally phosporylated tau, the microtubule binding protein. The neuritic plaque consists of a central core of amyloid β-protein (Aβ) fibrils surrounded by dystrophic neuritis (abnormal axons and dendrites). These plaques are extracellular, roughly spherical in shape, and range from about 5 $\mu$m to about 200 $\mu$m in diameter. The histopathological changes and neuronal loss are particularly severe in the hippocampus and medial temporal lobe, where the disease is believed to start, and in association areas of the neocortex. This regional selectivity determines the characteristic clinical feature of early memory loss. Whether tangles or plaques are more relevant to the pathogenesis of Alzheimer's disease is a matter of some debate.

Senile plaques are a more promising target than neurofibrillary tangles for visualizing with magnetic resonance imaging because they are extracellular and larger. To visualize even the largest plaques pushes MRI to its very limit. Conventional clinical magnetic resonance imaging employs magnets with field strengths ranging from about 0.5 T to about 1.5 T. With an acquisition time of less then seven minutes, a 1.5 T machine can image the entire brain with good grey matter/white matter contrast and a voxel size of 1 mm$^3$. In this way, small cerebral structures such as the hippocampus can be fairly reliably measured in vivo, and subfields of the hippocampus can be resolved. Plaques, however, are an order of magnitude smaller than the best depiction of brain structure achievable in vivo.

SUMMARY OF THE INVENTION

It is an object of the present invention to overcome the aforesaid deficiencies in the prior art.

It is another object of the present invention to provide an in vivo method for diagnosing Alzheimer's disease.

It is a further object of the present invention to detect amyloid plaques in vivo using magnetic resonance micro-imaging.

It is yet another object of the present invention to use labeled peptides for imaging preamyloid deposits and Congo red positive amyloid plaques.

It is another object of the present invention to provide a method for an early definite diagnosis of Alzheimer's disease.

It is still a further object of the present invention to provide a method for monitoring amyloid clearing in vivo.

The present invention provides a method for detecting the amyloid plaques characteristic of Alzheimer's disease using magnetic resonance micro-imaging ($\mu$MRI). The method uses A$\beta$-1-40 peptides, derivatives or mutants thereof or A$\beta$ homologous peptides which are labeled with a label that enhances the image in MRI. Particularly useful labels are gadolinium, manganese or monocrystalline iron oxide nanoparticles. One of these ligands is injected systemically with mannitol or another compound which acts as a carrier and transiently opens the blood-brain barrier so that the majority of both early pre-A$\beta$ deposits and Congo red positive amyloid plaques can be visualized.

An alternative strategy is to couple the labeled A$\beta$ peptide to a carrier molecule that more readily crosses the blood-brain barrier (BBB). This can be accomplished in three different ways:

1. The labeled-A$\beta$ peptide can have its lipid solubility increased by coupling the peptide to a cholesteryl group at the C- or N-terminus of the peptide (Bodor and Simpkins 1983; *Science*, 221: 65–67). Alternatively, the labeled-A$\beta$ peptide can be coupled to putrescine, which increases the lipid solubility and BBB passage (T. M. Wegenack, G. L. Curran, and J. F. Poduslo, *Nat. Biotech.* 18:868–872, 2000).

2. Chimeric peptidization can be used, in which the labeled-A$\beta$ peptide is coupled to a compound that has increased passage across the BBB, such as albumin (A. K. Kumagai, J. B. Eisenberg, and J. F. Poduslo, *J. Biol. Chem.* 262: 15214–15219, 1987).

3. The labeled-A$\beta$ peptide can be coupled to an antibody that targets a receptor on the BBB, such as the transferrin receptor. The antibody-labeled-A$\beta$ would then be carried across the BBB by transcytosis (W. M. Partridge, J. Buciak, and T. Yokishawa, *J. Pharmacol.* 269:66–70, 1991).

The method of the present invention makes it possible to diagnose Alzheimer's disease at an early stage so that treatment can be started as soon as possible to mitigate the damage. Additionally, the present invention permits monitoring of amyloid clearing in vivo.

BRIEF DESCRIPTION OF THE DRAWINGS

FIG. 2 shows that A$\beta$ plaques are detected with ex vivo $\mu$MRI after injection of Gd-DTPA-A$\beta$1-40 with mannitol.

FIG. 3 shows that A$\beta$ plaques are also detected with in vivo $\mu$MRI after injection of Gd-DTPA-A$\beta$1-40 with mannitol.

FIG. 4 shows several control experiments indicate the need for both magnetically-labeled Aβ1-40 and mannitol to detect Aβ plaques.

FIG. 5 shows that Aβ plaques are detected with ex vivo μMRI after injection of MION-Aβ1-40 with mannitol.

DETAILED DESCRIPTION OF THE INVENTION

Figure 1:
FIG. 1 shows a schematic representation of the synthesis and characterization of the two A$\beta$-specific-binding ligands for $\mu$MRI. A$\beta$1-40 was first synthesized with and without the chelating group, DPTA, on its amino terminus, followed by HPLC purification. The DPTA-A$\beta$1-40 was then used to chelate Gd, the Gd-DPTA-A$\beta$1-40 was repurified by HPLC and the expected mass verified by mass spectroscopy. Each DPTA-A$\beta$1-40 chelates a single Gd ion. Mass spectroscopy of the high pressure liquid chromatography (HPLC) purified Gd-DTPA-A$\beta$1-40 gave a mass 4975.76, in good agreement with expected mass of 4976.6. Alternatively, the A$\beta$1-40 was absorbed onto MION. $\square$MRI of the Gd-DTPA-A$\beta$1-40 and MION-A$\beta$1-40 at the same concentrations used for injection showed the expected T2-weighted signal loss and susceptibility effects of Gd-DTPA and MION, while unlabeled A$\beta$1-40 showed no T2-weighted signal effect. The A$\beta$1-40 alone, Gd-DPTA-A$\beta$1-40 or MION-A$\beta$1-40 were then injected with or without 15% mannitol in vivo into the carotid artery of wild-type, APP or APP/PS1 transgenic mice. Six hours after injection the mouse brains were imaged in vivo or ex vivo with $\mu$MRI.
Figure 1:
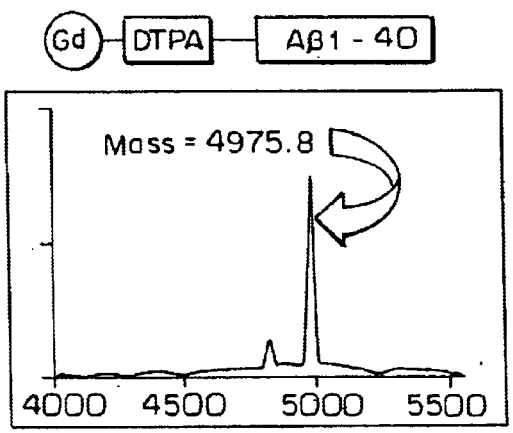
Figure 1:
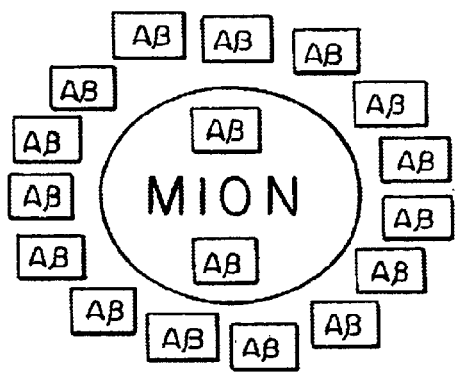
Figure 1:
Figure 1:
Figure 1:
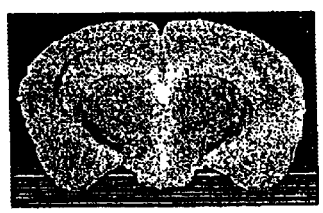

The present inventors previously demonstrated that 125I-Aβ1-40 injected into the carotid artery in a non-human primate binds to Aβ plaques as detected by autoradiography of brain sections (Mackic J B et al., General Pharmacology-Vascular System, in press). This finding supported in vitro studies that indicated that radiolabeled Aβ binds to Aβ plaques in vitro (Maggio et al., Proc. Natl. Acad. Sci. USA 89, 5462–5466 (1992)). Other studies have also shown that radiolabeled Aβ derivatives (Wengenack et al., Nat. Biotech. 18, 868–872 (2000)), or other radioactive probes that bind to AP (Skovronsky et al., Proc. Natl. Acad. Sci USA 97, 7609–7614 (2000)), allow the visualization of Aβ plaques following autoradiography of tissue sections.

The present inventors have discovered that plaques can be visualized in vivo by micro-magnetic resonance imaging (μMRI). By using a contrast agent that binds selectively to Aβ, plaques can be imaged under MRI conditions routinely used clinically.

The sequence of Aβ is as follows:

D A E F R H D S G Y E V H H Q K L V F F A E D V G S N K-GAIIGLMVGGVV (SEQ ID NO:1)

A number of compounds have been shown to bind Aβ, and the peptide itself (as well as Aβ homologous peptides) has a high binding affinity for other Aβ molecules (Jarrett et al., Cell 73, 55–1058 (1993); Wisniewski et al., Neurobiol. Dis. 4, 313–328 (1997)). Assembly of Aβ monomers results in Congo red positive fibrils which are the main component of the neuritic plaques in Alzheimer's disease. The present inventors have discovered that it is possible to use MRI to detect plaques following administration of Aβ bound to a contrast agent such as gadolinium, manganese, or monocrystalline iron oxide nanoparticles (MION). MION improves focal lesion detection because of enhanced imaging contrast properties. MION has a longer plasma half-life, stronger spin-spin relaxativity (R2), and larger induced magnetic susceptibility compared to clinically used gadolinium chelates.

The present inventors discovered that contrast agents such as gadolinium and manganese bound to the N-terminus of Aβ1-40, and that Aβ1-40 coated with MION particles can be used to image plaques in the brains of transgenic APP mice with Alzheimer's disease pathology. The majority of amyloid and pre-amyloid plaques were detected following systemic injection of the contrast agent, along with mannitol to transiently open the blood-brain barrier.

The present method for the in vivo diagnosis of Alzheimer's disease means that, once there is effective therapy for Alzheimer's disease, treatment may then begin before clinical symptoms occur, thereby possibly preventing the irreversible neuronal damage that eventually leads to dementia and ultimately death.

Aβ1-40 is the major sequence of all Aβ peptides found physiologically in biological fluids, with longer forms of Aβ peptides such as Aβ1-42 being more closely linked to the initiation of amyloid deposits and Alzheimer's disease related pathology. However, at high concentrations, Aβ1-40 has been found to be toxic in tissue culture, and Aβ1-40 is the major sequence of amyloid in vascular walls. Therefore, there is a potential for toxicity with use of these ligands, although there was no evidence of toxicity in the experiments described herein.

Rather than using the Aβ peptides per se, functional derivatives of these peptides can be used. By "functional derivative" is meant a fragment, variant, analog, or chemical derivative of the Aβ peptides, which terms are defined below. A functional derivative retains at least a portion of the amino acid sequence of the Aβ peptide, which permits its use in visualizing plaques related to Alzheimer's disease. Specificity can be readily quantified by determining the $IC_{50}$ according to Piersbacher et al., U.S. Pat. No. 5,648,330, the entire contents of which are hereby incorporated by reference.

A "fragment" of the Aβ peptide refers to any subset of the molecule, i.e., a shortened peptide. Peptides as small as five amino acids can be used, but these peptides should include the sequence of (residues 17–21 of SEQ ID NO:1) the Aβ peptide.

A "variant" of the Aβ peptide refers to a molecule which is substantially similar to either the entire peptide or a fragment thereof. Variant peptides can be conveniently prepared by direct chemical synthesis of the variant peptide, using methods well known in the art.

An "analog" of the Aβ peptide refers to a non-natural molecule which is substantially similar to the entire molecule or to an active fragment thereof.

A "chemical derivative" of the Aβ peptide contains additional chemical moieties not normally part of the Aβ amino acid sequence. Covalent modifications of the amino acid sequence are included within the scope of this invention. These modifications may be introduced into the Aβ peptides by reacting targeted amino acid residues from the peptide with an organic derivatizing agent that is capable of reacting with selected side chains or terminal residues.

Modifications of the Aβ sequence can be used to reduce the potential for fibrillogenesis, such as the addition of lysine (Lys), aspartate (Asp) praline (Pro) or glutamate (Glu) residues to the N- or C-terminus, or the substitution of residues within the 17–21 sequence (Leu-Val-Phe-Phe-Ala) of (SEQ ID:1) with Lys, Asp, Pro or Glu. Each of these modifications will reduce the ability of the Aβ to form fibrils, while still allowing the labeled-Aβ peptide to target amyloid lesions.

Alternatively, anti-Aβ antibodies are labeled with contrast agents. In fact, Gd labeling of antibodies has already been used to detect tumors in vivo.

Gd-Aβ1-40:

Phantom experiments, imaging the labeled peptide in solution, demonstrated the expected T1 enhancement, but a larger susceptibility effect was observed in both T2* and T2 imaging (see FIG. 1). Based on these observations, it was hypothesized that the presence of Gd-labeled Aβ peptide in Aβ plaques would lead to significant signal loss on T2*- and T2-weighted images. This was confirmed in preliminary experiments, where mice received Gd-Aβ1-40 directly into the brain parenchyma or intracerebroventricularily. In these mice the microMRI (μMRI) images clearly showed that the Gd-Aβ was able to diffuse from the site of injection and bind to existing amyloid deposits in vivo although the diffusion was mainly in the injected hemisphere (data not shown). A comparison of the MRI images with immunohistochemically stained brain sections using an anti-Aβ antibody confirmed that the numerous dark spots in the neocortex and hippocampus were indeed Aβ plaques (data not shown).

Figure 2B:
FIG. 2B shows a T2-weighted coronal $\mu$MR image matched to 2A, of an age-matched wild-type mouse brain, extracted 6 h after the injection of Gd-A$\beta$1-40 with 15% mannitol into the carotid artery. No focal dark lesions can be seen in any brain region of the control.
Figure 2D:
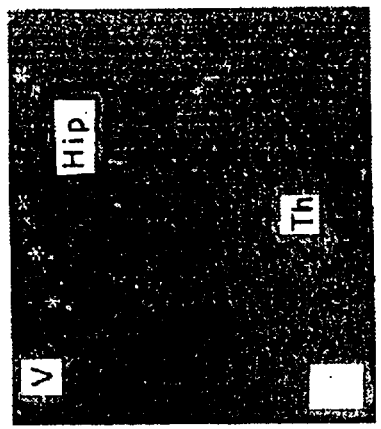
FIG. 2D shows the area enclosed in the box in 2C, was stained with Congo red and viewed under polarized light. Numerous yellow-green birefringent lesions are seen in the hippocampus (Hip) (asterix). However in the thalamus (Th), where many lesions are seen immunohistochemically with anti-A$\beta$ antibodies in C and corresponding lesions are seen by $\mu$MRI in A, very few Congo red positive lesions are evident. This indicates that the $\mu$MRI is able to detect at least some diffuse or preamyloid A$\beta$ lesions. Labels: V, dorsal third ventricle; Hip, Hippocampus and Th, Thalamus.
Figure 2A:
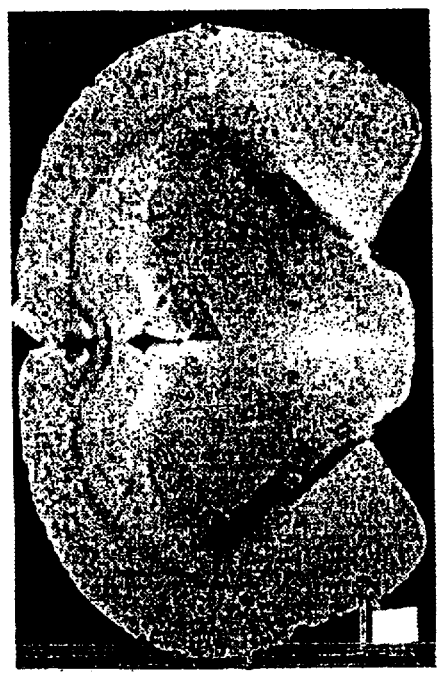
FIG. 2A shows a T2-weighted spin echo coronal $\mu$MR image of an APP/PS1 transgenic mouse brain, extracted 6 h after the injection of Gd-A$\beta$1-40 with 15% mannitol into its carotid artery shows numerous dark spots corresponding to amyloid. The red arrows indicate numerous lesions, which correspond to the anti-A$\beta$ immunohistochemistry seen in C.
Figure 2C:
FIG. 2C shows an approximate matching tissue section to 2A, immunoreacted with 6E10 (monoclonal anti-A$\beta$) demonstrates numerous lesions which correspond to the dark spots on $\mu$MRI (arrows). A portion of the left dorsal cortex was removed for identification.

These promising early findings led the inventors to determine if one could visualize these plaques following a systemic injection in APP and PS1/APP Tg mice. FIG. 2A shows a T2*-weighted SE (TR=500 msec, TE=15 ms, FA=43°) coronal image of a PS1/APP mouse brain, acquired 6 hours after the injection of Gd-Aβ1-40 with 15% mannitol into the common carotid artery. Numerous dark spots can be seen in the transgenic mouse brains (FIG. 2A). None of the control animals exhibited similar dark spots in the regions with amyloid (FIG. 2B). Indeed, using a variety of MRI signal sequences it has not been possible to image amyloid, without the injection of an amyloid ligand, in aged PS1/APP or APP Tg mice. Many of the dark spots in the Gd-Aβ injected mice (FIG. 2A) showed good correlation with the corresponding immunohistochemically stained brain sections for amyloid (FIG. 2C). However, the match is not exact since the μMRI slice thickness is 150 μm, while the histology section is 40 μm. Furthermore, it was not possible to obtain exactly the same plane of section in the histology and μMRI. T2*-SE gave a higher signal to noise ratio (SNR) in a shorter imaging time ($T_{IM}$=35 min., SNR=83) than T2-SE ($T_{IM}$=137, SNR=62) and both provided equivalent lesion detection. Amyloid lesions were not observed in T1-weighted SE images (TR=250 ms, TE=10 ms) of the same mouse brain (data not shown), because the T1-weighted images presented poor anatomical detail and low tissue contrast. Although T1-enhancement was observed at the injection site (in mice subjected to direct intra-cerebral injections), there was no apparent enhancement in the histologically detected lesions (data not shown). It is speculated that this lack of lesion detection by T1-SE may be due to an antagonism between T1 and susceptibility effects. Sequential tissue sections were also subjected to Congo red staining for amyloid. As can be seen in FIG. 2D, some of the amyloid deposits in the thalamus, which could be detected by μMRI and anti-Aβ immunohistochemistry did not show the characteristic apple-green birefringence, under polarized light. This indicates that μMRI was able to detect early diffuse or preamyloid lesions.

Figure 3B:
FIG. 3B shows an approximate matching tissue section to 3A, immunoreacted with 6E10 (monoclonal anti-A$\beta$) demonstrates numerous lesions which correspond to the $\mu$MRI in A (arrows).
Figure 3D:
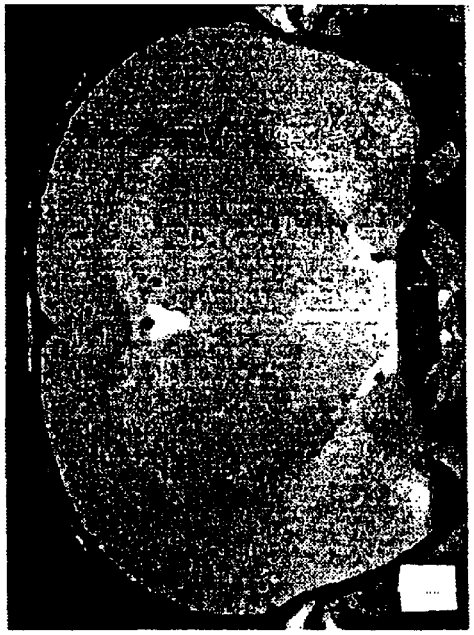
FIG. 3D shows In vivo T2-weighted coronal $\mu$MR image matched to 3A, of an age-matched wild-type mouse brain treated in the same manner as the transgenic mouse shown in A. Focal dark lesions corresponding to amyloid are not detected.
Figure 3A:
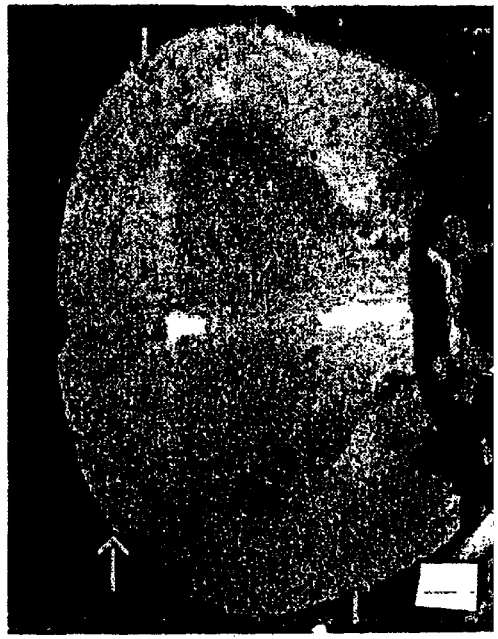
FIG. 3A shows In vivo T2-weighted spin echo coronal $\mu$MR image of an anesthetized APP/PS1 transgenic mouse brain, 6 h after the intra-carotid injection of Gd-DTPA-A$\beta$1-40 with 15% mannitol showing numerous dark spots corresponding to amyloid (arrows).
Figure 3C:
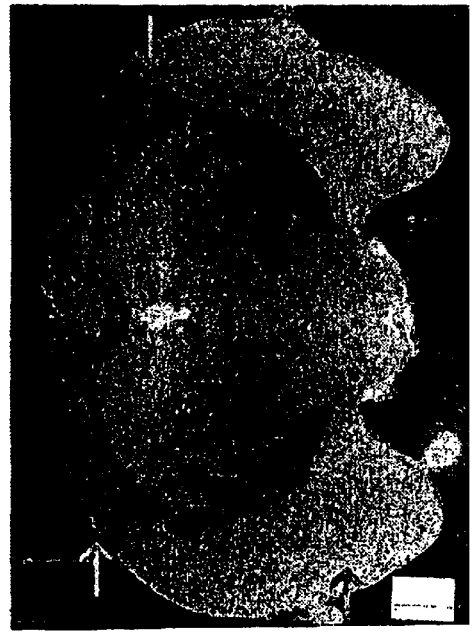
FIG. 3C shows an Ex vivo T2-weighted spin echo coronal MR image of the same APP/PS1 mouse brain seen in 3A and 3B. The mouse was sacrificed immediately following the in vivo imaging seen in 3A and the brain was embedded, followed by $\mu$MRI. Numerous dark spots corresponding to amyloid can be seen, some of which co-register with lesions evident in A and B (arrows).
Figure 4A:
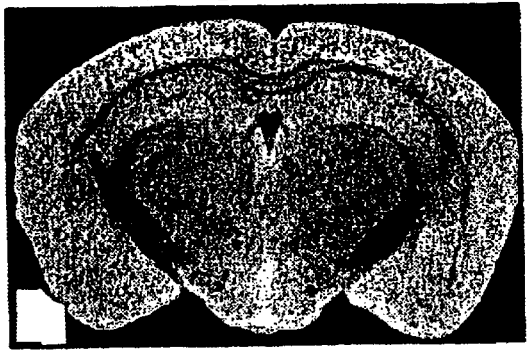
FIG. 4A shows T2-weighted spin echo coronal μMR image of an uninjected 16 month old APP transgenic mouse shows no cortical lesions.
Figure 4B:
FIG. 4B shows a corresponding tissue section, immunoreacted with 6E10 (monoclonal anti-AD) shows numerous amyloid plaques, which were not detected in A.
Figure 4C:
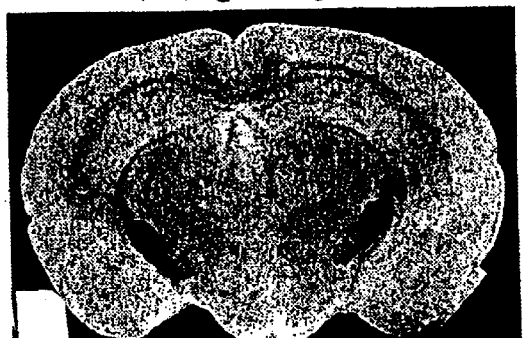
FIG. 4C shows T2-weighted spin echo coronal μMR image of a 16 month old APP transgenic mouse injected with MION-Aβ1-40 alone, without mannitol shows no cortical lesions.
Figure 4D:
FIG. 4D shows a corresponding tissue section, immunoreacted with 6E10 shows numerous amyloid plaques, which were not detected in C.
Figure 4E:
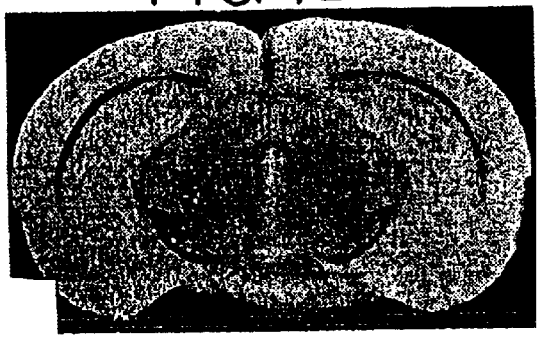
FIG. 4E shows a T2-weighted spin echo coronal μMR image of a 16 month old APP transgenic mouse injected with Gd-DTPA-Aβ1-40 alone, without mannitol shows no cortical lesions.
Figure 4F:
FIG. 4F shows a corresponding tissue section, immunoreacted with 6E10 shows numerous amyloid plaques, which were not detected in E.

The present inventors have demonstrated that it is possible to perform imaging in vivo, as can be seen in FIGS. 3A and 3B. The method of the present invention made it possible to image the majority of amyloid plaques in vivo in mice injected with Gd-Aβ.

Figure 5A:
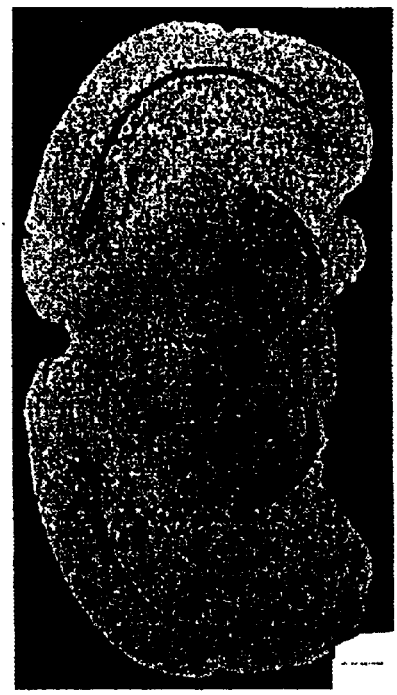
FIG. 5A shows a T2-weighted spin echo coronal μMR image of a 15 month old APP transgenic mouse brain, extracted 6 h after the carotid injection of MION-Aβ1-40 with 15% mannitol, shows numerous dark spots corresponding to amyloid. The red arrows indicates lesions which correspond to the anti-Aβ immunohistochemistry in C.
Figure 5B:
FIG. 5B shows a T2-weighted coronal μMR image matched to 5A, of an age-matched wild-type mouse brain, extracted 6 h after the carotid injection of MION-Aβ1-40 with 15% mannitol. No focal dark lesions were seen within the brain of the control mouse.
Figure 5C:
FIG. 5C shows an approximate matching tissue section to 5A, immunoreacted with 6E10 (monoclonal anti-Aβ). Numerous lesions can be seen which correspond to the μMRI in A (arrows). The insert shows an adjacent section stained with Congo red revealing the Aβ amyloid plaque staining.
Figure 5D:
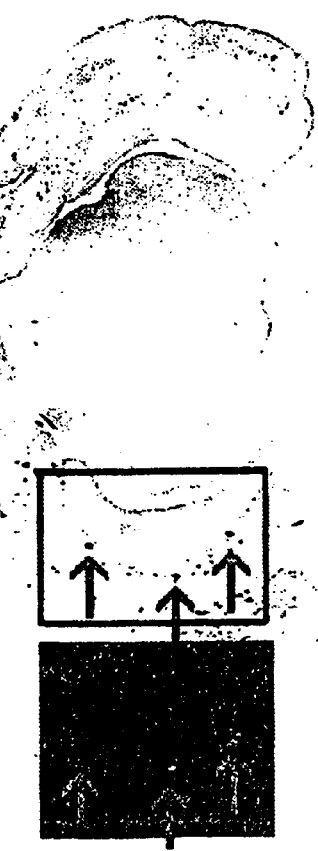
FIG. 5D shows a high power view of an amyloid plaque in a sequential section to 5A and 5C, double stained with 6E10 antibodies (brown color) and a Mallory stain for iron (arrow, azure color) demonstrating the co-localization of the MION-Aβ with Aβ amyloid plaques. Scale bar corresponds to 35 μm.

MION-Aβ:

The MION-AP co-injected with 15% mannitol in APP Transgenic mice also allowed visualization of a majority of the amyloid lesions in Tg mice (FIGS. 5A and 5C). The percentage of plaques detected appeared to be similar to those observed with Gd-Aβ1-40. No plaques were observed in non-Tg mice that received MION-Aβ or MION alone (FIG. 5B). The co-deposition of the MION-Aβ on amyloid lesions was confirmed histologically by double staining with a Mallory stain (for iron giving an azure color) and amyloid immunohistochemistry, using diaminobenzidine (DAB) to produce a brown color (FIG. 5D).

In all mice the percentage of amyloid lesions seen on the μMRI and by immunohistology was correlated. In each of these animals, the cortical amyloid burden in the right cerebal hemisphere following immunostaining with anti-Aβ monoclonal antibody 6E10, was determined by standard unbiased stereology with a Bioquant imaging system attached to a fluorescent Leica DMLB microscope. Sequential tissue sections were also stained with Congo red, in order to determine if the Aβ immunoreactive lesions were amyloid or preamyloid. The area analyzed was dorsomedial from the cingulate cortex and extended ventro-laterally to the rhinal fissure within the right hemisphere. The area of the grid was 1200×800 $\mu m^2$ and the amyloid load was measured in 10 frames per mouse (each: 640×480 $\mu m^2$) in 5 randomly chosen sections. For the μMRI, circular dark areas of contrast within the same anatomical landmarks, which corresponded to Aβ immunoreactivity were counted as "amyloid". Since the μMRI slice thickness was from 150 μm to 500 μm and histology slice thickness was 40 μm, each μMRI was compared to several histological sections. Using this criteria, in mice that received direct intra-carotid injections of 15% mannitol solution containing Gd-Aβ1-40 or MION-Aβ, the majority (>80%) of all amyloid lesions could be visualized. Some of the areas visualized by μMRI were not evident by Congo red staining, suggesting that the μMRI can also detect preamyloid lesions. This can be appreciated in FIGS. 2A and 2D where numerous lesions can be seen in the right thalamus by μMRI (FIG. 2A), a region where most of the Aβ deposits are Congo red negative (FIG. 2D).

Experimental Protocol:

Peptide and contrast agents: Aβ1-40 and Aβ1-40 containing a metal chelating arm were synthesized on a ABI 430A peptide synthesizer using standard protocols for tBOC (tert-butyloxycarbonyl) chemistry. The chelating arm, diethylentriaminepentaacetic acid (DTPA), was attached to the amino terminus of the peptide as the final step of synthesis. The peptides were cleaved from the resins using hydrofluoric acid and purification was performed by high pressure liquid chromatography (HPLC) on a Vydac C18 preparative column, 2.5×30 cm (Vydac Separations, Hesperia, Calif.), using linear gradients from 0–70% of acetonitrile in 0.1% trifluoroacetic acid. Gadolinium (Gd) was chelated to the DTPA-Aβ peptide using Gd (III) chloride hexahydrate (Aldrich, Milwaukee Wis., 27,852-1) with a 24 h incubation in water at pH 7.0. The Gd-DTPA-Aβ1-40 complex was then purified using the procedure described above and the peptide was lyophilized. Mass spectroscopy of the HPLC purified Gd-DTPA-Aβ1-40 gave a mass of 4975.76, in agreement with the expected mass of 4976.6. Analytical HPLC showed a purity of >90–95%, and the molar ratio of the Aβ1-40 to Gd was 1:1. The purification and characterization for standard Aβ1-40 gave similar results for the expected molecular weight and purity.

Monocrystalline iron oxide nanoparticles (MION) were obtained from the Center for Molecular Imaging Research (Massachusetts General Hospital, Boston, Mass.) as a brownish, stock solution with 12.05 mg Fe/ml. Each MION particle contains an average of 2,064 Fe molecules. For injection into each mouse, 300 µg of dextran-coated MION particles (15.8 µl of stock solution), was adsorbed with 120 µg of Aβ1-40 in a volume of 120 µl of $H_2O$ by overnight mixing at 4° C. Following this incubation, the Aβ1-40 remained in solution. To determine the effectiveness of the Aβ1-40 absorption onto the MION, the mixture was centrifuged at 100,000 g for 40 min in a Beckman TL-100 ultracentrifuge. This produced a clear supernatant and a brownish lower phase. HPLC analysis revealed that >99% of the Aβ1-40 and MION were found in the lower phase. In control experiments incubating Aβ1-40 alone for 24 h, the peptide did not pellet at 100,000 g, but remained in solution. We calculated that 17 Aβ1-40 molecules were bound to each nanoparticle of MION-Aβ1-40.

MRI System: µMRI experiments were performed on a SMIS console interfaced to a 7 Tesla horizontal bore magnet equipped with 250 mT/m actively shielded gradients (Magnex Scientific, Abingdon UK). Preliminary imaging experiments were performed to assess the relaxivity effects of unlabeled, Gd-labeled and MION-labeled peptides in a water solution (FIG. 1).

Ex vivo µMR imaging of fixed tissues was used initially to determine the feasibility of the magnetic labeling approach, as in previous seminal reports on the development of µMRI methods for cell tracking and imaging transgene expression. For ex vivo µMRI, extracted whole mouse brains were embedded in 3% aqueous agarose gel to prevent dehydration during µMRI. The sample temperature was maintained at 20° C. using a water circulating system that also controls the temperature of the magnet bore. A custom 3-turn solenoid coil (ID=16 mm) was developed to fit closely around fixed mouse brain samples during ex vivo µMRI. For each brain, 11 contiguous coronal image slices were acquired from the olfactory bulb to the cerebellum, with 59 µm×59 µm in-plane resolution and a slice thickness of 500 µm. A T2-weighted pulse sequence (echo time, TE=50 ms; repetition time, TR=2 s; total imaging time=136 minutes) was used to image each brain sample. This approach provided an acceptable compromise between good anatomical detail and soft tissue contrast, with sufficient susceptibility effect to allow reliable detection of contrast agent accumulation in plaques in the brains of the transgenic mice.

For in vivo µMRI the mice were initially anesthetized with isoflurane (5%) in air, and anesthesia was maintained with 1.5% isoflurane in air (2 1/min flow rate). The rectal temperature and respiratory rate of each mouse were monitored throughout the scan. A custom saddle coil (ID=22 mm) was incorporated into the holding device, and a tooth bar used to fix the head in a reproducible and stationary position during data acquisition. As in the ex vivo imaging protocol, 11 contiguous 500 µm thick coronal brain image slices were acquired for each mouse, using a T2-weighted pulse sequence (TE=50 ms; TR=2 s; 78 µm×78 µm in-plane resolution; total imaging time=120 minutes).

Mice and Contrast Agent Injection: Gd-DTPA-Aβ1-40 was prepared before each administration by suspending 400 µg in 100 µl water and dissolving immediately before infusion with a solution of 15% mannitol in PBS (600 µl), in order to temporarily open the BBB. This preparation was injected directly into the common carotid artery at a rate of 0.25 ml/kg/sec. This rate is below that which causes hypertensive opening of the BBB, but gives optimal BBB disruption without neurotoxicity. This dosage of Gd-DTPA-Aβ1-40 represents a much smaller dose of Gd-DTPA per body weight than is used in a typical human clinical study (0.2 ml/kg). This human dose corresponds to 472 µg of Gd, whereas we used 12.6 µg of Gd per mouse (400 µg×157.25/4976), or approximately 3% of the human dose. A higher dosage of Gd-DTPA-Aβ1-40 could not be used since 400 µg in a 700 µl total volume was at the limit of solubility of this peptide.

In other experiments MION-Aβ1-40 was used as the contrast agent. In this case each mouse received 300 µg of MION particles, on to which 120 µg of Aβ1-40 was absorbed (as described above; corresponding to 190 mgFe/kg). The dosage of MION reported in human studies has ranged between 1.1 and 2.6 mgFe/kg; hence, the mice received a substantially higher dose. Immediately before injection into the common carotid artery, MION-Aβ1-40 was mixed with 600 µl of 15% mannitol in PBS.

Both Gd-DTPA-Aβ1-40 and MION-Aβ1-40 were co-injected with mannitol into 6-month old APP/PS1 transgenic mice, 15–16 month old APP transgenic mice, as well as age-matched, non-transgenic controls (Table 1). A number of additional control experiments were also performed, injecting Gd-DTPA-Aβ1-40 without mannitol, Gd-DTPA with mannitol but without Aβ1-40, or no injection. Six hours after intra-carotid injection, the mice were either imaged in vivo or anesthetized with sodium pentobarbital (150 mg/kg, i.p.), perfused transaortically with 0.1 M phosphate buffer, pH 7.4, and 4% paraformaldehyde in phosphate buffer as described previously. Six hours was chosen as a time point since our own and other studies using $^{125}I$-Aβ1-40 have shown that the time of maximum AD plaque labeling following systemic injections, with minimal non-specific labeling of blood vessels, is between 4–6 h. The brains were kept in fixative overnight before being embedded in 3% agarose for imaging. Imaging of fixed brains was done because the unfixed brains were more likely to become distorted during removal and embedding in agarose and would deteriorate significantly during the embedding and imaging procedures, compromising subsequent immunohistochemical analysis. In addition, the slight shrinkage of the brain following fixation facilitated the matching to the histology sections, which are also subject to shrinkage.

Histology:

Following imaging, the brains were placed in 2% DMSO/20% glycerol in 0.1M phosphate buffer, pH 7.4, overnight. Subsequently, coronal sections (40 µm) were cut and serial sections at 0.2 mm intervals were saved for histological analysis of 1) 6E10, 2) Congo red or 3) Mallory stained sections. 6E10 recognizes Aβ. Congo red staining was performed to distinguish amyloid from preamyloid Aβ immunoreactive deposits. The Mallory iron-staining method enabled us to detect MION particles associated with the Aβ plaques. The series were placed in ethylene glycol cryoprotectant and stored at −20° C. until used.

Congo red: Mounted sections were defatted in Hemo-De and hydrated in a gradient of ethyl alcohol and water series. Congo red staining was performed as previously described.

6E10: Staining was performed as previously described. Briefly, sections were incubated in 6E10 (Senetek) at a 1:1000 dilution. A mouse on mouse immunodetection kit (Vector Laboratories) was used where the anti-mouse IgG secondary antibody was used at a 1:2000 dilution. The sections were reacted in 3,3'-diaminobenzidine tetrahydrochloride (DAB) with or without nickel ammonium sulfate intensification.

Mallory: The Mallory method for iron was performed by placing defatted and hydrated sections for 10 minutes in a solution containing 2.5% potassium ferrocyanide and 2.5% hydrochloric acid. The slides were then rinsed in distilled water, the sections dehydrated, cleared in Hemo-De, mounted and cover slipped.

Amyloid Burden Quantitation: Immunohistochemistry of tissue sections was quantified with a Bioquant stereology image analysis system (R&M Biometrics Inc., Nashville, Tenn.) using unbiased sampling. The cortical area analyzed was dorsomedially from the cingulate cortex and extended ventrolaterally to the rhinal fissure within the right hemisphere. The area of the grid was 800×800 $\mu m^2$ and amyloid burden was measured in 12 frames per mouse (each: 640× 480 $\mu m^2$), chosen randomly. The Aβ burden is defined as the percent of area in the measurement field occupied by reaction product.

For quantitation of the amyloid burden in $\mu$MRI images, digitized tagged-image format files with a calibrated spatial resolution were imported into the Bioquant stereology image analysis software. The brightness of the images was altered so that the average optical density measurement for each imported image was similar. A region of interest was manually drawn on the cortex corresponding to the anatomical landmarks used for the histological amyloid burden quantification. The anatomic locations and boundaries of the cortical region analyzed were based on those defined by Franklin and Paxinos. Dark spots within this region of interest that had a threshold value below 110 and individually corresponded to an area between 100 and 900 $\mu m^2$ were counted as "amyloid". The amyloid burden was calculated as the percentage of area occupied by dark spots within the defined cortical region, after thresholding. The amyloid burden quantification was performed by an individual blinded to the genotype of the mice and the experimental protocol used.

A majority of parenchymal amyloid deposits can be detected using a contrast agent co-injected with a compound such as mannitol or a carrier molecule compound which transiently increases blood-brain barrier permeability in both animal and human studies. Despite the known high permeability of Aβ1-40 via receptor mediated transport, no lesions were detected when either the Gd-Aβ or MION Aβ were injected without mannitol, suggesting that a carrier is necessary to transport the Aβ across the blood-brain barrier. This is to be expected, as it is well documented that neither gadolinium nor MION crosses the blood-brain barrier. In addition to gadolinium, manganese can be used as a contrast agent. Since no known contrast agents are capable of crossing the blood-brain barrier, these contrast agents must be used in conjunction with a carrier molecule to transport the contrast agent over the BBB.

The need for a compound that transiently opens the blood-brain barrier does not preclude the use of these amyloid ligands in humans, since this method for transiently opening the blood-brain barrier has been safely used in conjunction with chemotherapy to treat human brain tumors, as well as for other clinical purposes. Congo red positive lesions, as well as "preamyloid" or diffuse plaques, can be detected using these amyloid ligands.

Preamyloid lesions are thought to represent early, non-fibrillar forms of parenchymal brain Aβ deposition, which over time develop into neuritic plaques that are associated with neuronal damage. Preamyloid lesions do not stain with Congo red. However, as shown in FIGS. 2A–2D, at least some preamyloid lesions can be labeled and visualized by the method of the present invention. As shown in FIGS. 2A–2D, a number of lesions were labeled with the gadolinium-Aβ 1-40 in the right thalamus and both hippocampi, which are also evidenced by immunohistochemical staining with anti-Aβ antibodies (FIG. 2C). However, on Congo red staining of sequential sections (FIG. 2D), several amyloid lesions could be seen to have the characteristic apple-green birefringence of amyloid in the right hippocampus, but most of the Aβ deposits in the right thalamus did not stain with the Congo red. The presence of preamyloid deposits has previously been noted in the thalamus and striatum of these aged Alzheimer's Tg mice, (McGowan et al., *Neurobiol. Dis.* 6, 231–244 (1999)). Thus, the process of the present invention permits early detection of amyloid lesions, when they may be most amenable to therapeutic intervention. Additionally, the present invention makes it possible to monitor amyloid clearing in vivo.

The foregoing description of the specific embodiments will so fully reveal the general nature of the invention that others can, by applying current knowledge, readily modify and/or adapt for various applications such specific embodiments without undue experimentation and without departing from the generic concept. Therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying our various disclosed functions make take a variety of alternative forms without departing from the invention. Thus, the expressions "means to . . . ' and "means for . . . " as may be found in the specification above and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above; and it is intended that such expressions be given their broadest interpretation.

REFERENCES

1. Morris, et al., (1996) *Neurol.* 46, 707–719.
2. Morris, (1999) *J. Clin. Invest.* 104, 1171–1173.
3. Schenk, et al., (1999) *Nature* 400, 173–177.
4. Sigurdsson, et al., (2000) *J. Neuropath. Exp. Neurol.* 59, 11–17.
5. Bard, et al., (2000) *Nature Med.* 6, 916–919.
6. Weiner, et al., (2000) *Ann. Neurol.* 48, 567–579.
7. Maggio, et al., (1992) *Proc. Natl. Acad. Sci. USA* 89, 5462–5466.
8. Wengenack, et al., (2000) *Nat. Biotech.* 18, 868–872.
9. Skovronsky, et al., (2000) *Proc. Natl. Acad. Sci. USA* 97, 7609–7614.

10. Bacskai, et al., (2001) *Nat. Med.* 7, 369–372.
11. Benveniste, et al., (1999) *Proc. Natl. Acad. Sci. USA* 96, 14079–14084.
12. Jarrett, et al., (1993) *Cell* 73, 1055–1058.
13. Wisniewski, et al., (1997) *Neurobiol. Dis.* 4, 313–328.
14. Zlokovic, et al., (1994) *Biochem. Biophys. Res. Commun.* 205, 1431–1437.
15. Mackic, et al., (1998) *J. Clin. Invest.* 102, 734–743.
16. Posuslo, et al., (1997) *Neurobiol. Dis.* 4, 27–34.
17. Kuriashkin, et al., (2000) *Veterinary Radiology & Ultrasound* 41, 4–7.
18. Stark, et al., (1999) *Magnetic resonance imaging.* (Mosby, St. Louis).
19. Shen, et al., (1993) *Magn. Reson. Med.* 29, 599–604.
20. Lewin, et al., (2000) *Nat. Biotech.* 18, 410–414.
21. Marecos, et al., (2000) *Radiology* 214, 568–574.
22. Weissleder, et al., (2001) *Nat. Med.* 6, 351–354.
23. Moore, et al., (1997) *J. Magn. Reson. Imaging* 7, 1140–1145.
24. Xu, et al., (1998) *J. Neurosci. Res.* 52, 549–558.
25. Hsiao, et al., (1996) *Science* 274, 99–102.
26. Holcomb, et al., (1998) *Nat. Genet.* 4, 97–100.
27. Siegal, et al., (2000) *J. Neurosurg.* 92, 599–605.
28. Chi, et al., (1997) *Anesth. Analg.* 84, 370–375.
29. Cosolo, et al., (1989) *Am. J. Physiol.* 256, R443-R447.
30. Sigurdsson, et al., (1996) *Neurobiol. Aging* 17, 893–901.
31. Wengenack, et al., (2000) *Nat. Biotech.* 18, 868–872.
32. Mackic, et al., (2002) *Gen. Pharmacol. Vasc. Sys.* in press.
33. Bellin, et al., (2000) *Eur. J. Rad.* 34, 257–264.
34. Enochs, et al., (1999) *J. Magn. Reson. Imaging* 9, 228–232.
35. Harisinghani, et al., (2001) *J. Comp. Ass. Tomogr.* 25, 770–776.
36. Harisinghani, et al., (1999) *Am. J. Roent.*, 1347–1351.
37. Harisinghani, et al., (1997) *J. Magn. Reson. Imaging* 7, 161–163.
38. Nguyen, et al., (1999) *J. Magn. Reson. Imaging* 10, 468–473.
39. Kim, et al., (1990) *Neurosci. Res. Comm.* 7, 113–122.
40. Sigurdsson, et al., (1997) *Neurobiol. Aging* 18, 591–608.
41. Soto, et al., (1998) *Nat. Med.* 4, 822–826.
42. Irizarry, et al., (1997) *J. Neurosci.* 17, 7053–7059.
43. Sigurdsson, et al., (2001) *Am. J. Pathol.* 159, 439–447.
44. Franklin, et al., (1997) *The mouse brain in sterotaxic coordinates.* (Academic Press, London).
45. Golabek, et al., (1996) *J. Bio. Chem.* 271, 10602–10606.
46. Golabek, et al., (2000) *Biophys. J.* 79, 1008–1015.
47. Masters, et al., (1985) *Proc. Natl. Acad. Sci. USA* 82, 4245–4249.
48. Irizarry, et al., (1997) *J. Neuropath. Exp. Neurol.* 56, 965–973
49. Takeuchi, et al., (2000) *Am. J. Pathol.* 157, 331–339.
50. Wengenack, et al., (2000) *Neurosci.* 101, 939–944.
51. Curran, et al., (1996) Permeability and residual plasma volume of human dutch variant and rat amyloid β-protein at the BBB. Society for Neuroscience Abstracts 22 (Part 2), 1168.
52. Poduslo, et al., (1999) *Neurobiol. Dis.* 6, 190–199.
53. Sell, (2000) in *Neuroimaging* (W. B. Saunders Co., London) 469–486.
54. Kroll, et al., (1998) *Neurosurgery* 42, 1083–1100.
55. Witt, et al., (2001) *Peptides* 22, 2329–2343.
56. Selkoe, (2000) *JAMA* 283, 1615–1617.
57. McGowan, et al., (1999) *Neurobiol. Dis.* 6, 231–244.
58. Vigo-Pelfrey, et al., (1993) *J. Neurochem* 61, 1965–1968.
59. Haass, et al., (1992) *Nature* 359, 322–325.
60. Younkin, (1995) *Ann. Neurol.* 37, 287–288.
61. Kowall, et al., (1992) *Neurobiol. Aging* 13, 537–542.
62. Prelli, et al. (1988) *J. Neurochem.* 51, 648–651.
63. Soto, et al., (1996) *J. Biol. Chem.*
64. Sigurdsson, et al., (2001) *Am. J. Pathol.* 159, 439–447.
65. Curtet, et al., (1998) *Investigative Radiology* 33, 752–761.
66. Gupta, et al., (1996) *Magn. Reson. Imag. Clin. N. Amer.* 4, 171–184.

What is claimed is:

1. A method for diagnosing Alzheimer's disease in vivo comprising injecting a labeled Aβ peptide, fragment, variant, analog, or chemical derivative thereof which has substantially the same activity as the Aβ peptide into a patient to be diagnosed and imaging preamyloid deposits and plaques using micro-magnetic resonance imaging.

2. The method according to claim 1 wherein the Aβ peptide is Aβ1-40.

3. The method according to claim 1 wherein the Aβ peptide is Aβ1-40.

4. The method according to claim 1 wherein the Aβ peptide comprises residues 17-21 of (SEQ ID NO:1) of Aβ1-40.

5. The method according to claim 1 wherein the Aβ peptide comprises a sequence of the full length Aβ peptide containing at least five amino acids.

6. The method according to claim 1 wherein a compound which transiently opens the blood-brain barrier is injected along with labeled Aβ peptide.

7. The method according to claim 6 wherein the compound which transiently opens the blood-brain barrier is mannitol.

8. The method according to claim 1 wherein the label is selected from the group consisting of gadolinium, manganese, and monocrystalline iron oxide nanoparticles.

9. The method according to claim 1 wherein the labeled peptide is coupled to a carrier molecule that crosses the blood-brain barrier.

10. The method according to claim 9 wherein the carrier molecule includes a cholesteryl group.

11. The method accruing to claim 1 wherein the carrier molecule is putrescine.

12. The method according to claim 1 wherein the labeled peptide is coupled by chimeric peptidization to a compound which crosses the blood-brain barrier.

13. The method according to claim 12 wherein the compound is albumin.

14. The method according to claim 1 wherein the labeled Aβ peptide is coupled to an antibody that targets a receptor on the blood-brain barrier.

15. The method according to claim 14 wherein the antibody is an antibody for the transferrin receptor.

16. The method according to claim 1 wherein the AB peptide is selected from the group consisting of Aβ1-40, Leu-Val-Phe-Phe-Ala of (SEQ ID NO:1), and modified Aβ1-40.

17. A method for monitoring amyloid clearing comprising injecting a labeled Aβ peptide, fragment, variant, analog, or chemical derivative thereof into a patient to be monitored and imaging preamyloid deposits and plaques using micromagnetic resonance imaging.

18. The method according to claim 17 wherein the Aβ peptide is Aβ1-40.

19. The method according to claim 17 wherein the Aβ peptide is Aβ1-40.

20. The method according to claim 17 wherein the Aβ peptide comprises residues 17-21 of (SEQ ID NO:1) of Aβ1-40.

21. The method according to claim 17 wherein the Aβ peptide comprises a sequence of the full length Aβ peptide containing at least five amino acids.

22. The method according to claim 17 wherein a compound which transiently opens the blood-brain barrier is injected along with labeled Aβ peptide.

23. The method according to claim 22 wherein the compound which transiently opens the blood-brain barrier is mannitol.

24. The method according to claim 17 wherein the label is selected from the group consisting of gadolinium, manganese, and monocrystalline iron oxide nanoparticles.

25. The method according to claim 17 wherein the labeled peptide is coupled to a carrier molecule that crosses the blood-brain barrier.

26. The method according to claim 25 wherein the carrier molecule includes a cholesteryl group.

27. The method accruing to claim 25 wherein the carrier molecule is putrescine.

28. The method according to claim 25 wherein the labeled peptide is coupled by chimeric peptidization to a compound which crosses the blood-brain barrier.

29. The method according to claim 28 wherein the compound is albumin.

30. The method according to claim 25 wherein the labeled Aβ peptide is coupled to an antibody that targets a receptor on the blood-brain barrier.

31. The method according to claim 30 wherein the antibody is against the transferrin receptor.

32. method according to claim 17 wherein the Aβ peptide is Aβ1-40 with the addition of at least one amino acid selected from the group consisting of lysine, aspartate or glutamate.

33. The method according to claim 25 wherein the Aβ peptide is selected from the group consisting of Aβ1-40, Leu-Val-Phe-Phe-Ala of (SEQ ID NO:1), and modified Aβ1-40.

34. The method according to claim 33 wherein the Aβ peptide is Aβ1-40 with the addition of at least one amino acid selected from the group consisting of lysine, aspartate or glutamate.

35. The method according to claim 1 wherein the Aβ peptide is Leu-Val-Phe-Phe-Ala of (SEQ ID NO:1) wherein at least one of the amino acids in the peptide is substituted by at least one amino acid selected from the group consisting of Lys, Pro, Asp, and Glu.

36. The method according to claim 33 wherein the Aβ peptide is Leu-Val-Phe-Phe-Ala of (SEQ ID NO: 1) wherein at least one of the amino acids in the peptide is substituted by at least one amino acid selected from the group consisting of Lys, Pro, Asp, and Glu.

* * * * *